US010751142B1

(12) United States Patent
Rosendahl (10) Patent No.: US 10,751,142 B1
(45) Date of Patent: Aug. 25, 2020

(54) DEVICE FOR HOLDING A DRAIN OR GUTTER DOWNSPOUT EXTENSION (71) Applicant: Robert Rosendahl, Menomonie, WI (US)

(72) Inventor: Robert Rosendahl, Menomonie, WI (US)

(*) Notice: Subject to any disclaimer, the term of this patent is extended or adjusted under 35 U.S.C. 154(b) by 0 days.

(21) Appl. No.: 16/181,446

(22) Filed: Nov. 6, 2018

Related U.S. Application Data (63) Continuation of application No. 15/932,745, filed on Apr. 18, 2018.

(51) Int. Cl.
A61B 50/00 (2016.01)
A61B 50/39 (2016.01)
B09B 3/00 (2006.01)
A61B 50/36 (2016.01)
A61B 50/37 (2016.01)
A61M 5/32 (2006.01)
A61L 11/00 (2006.01)

(52) U.S. Cl.
CPC ............ A61B 50/39 (2016.02); A61B 50/362 (2016.02); B09B 3/0075 (2013.01); A61B 50/37 (2016.02); A61L 11/00 (2013.01); A61M 5/3205 (2013.01)

(58) Field of Classification Search
CPC ..... E04D 13/08; E04D 13/076; E04D 13/064; E04D 13/0645
USPC .................. 248/87, 48.1, 49, 65, 74.3; 52/16
See application file for complete search history.

(56) References Cited

U.S. PATENT DOCUMENTS

| 3,572,622 | A | * | 3/1971 | Smith | F16L 1/0246 248/49 |
| 6,012,682 | A | * | 1/2000 | Tredennick | E04D 13/08 248/48.1 |
| 6,823,894 | B1 | * | 11/2004 | Koller | E03F 1/002 137/615 |
| 7,739,839 | B1 | * | 6/2010 | Crabtree | E04D 13/08 138/96 R |
| 9,399,849 | B2 | * | 7/2016 | Langenderfer | E02D 5/80 |
| 2007/0204522 | A1 | * | 9/2007 | Tredennick | E04D 13/08 52/12 |
| 2011/0173897 | A1 | * | 7/2011 | Schneider | E04D 13/08 52/16 |
| 2014/0284433 | A1 | * | 9/2014 | Gazlay | F16L 1/0246 248/87 |

* cited by examiner

Primary Examiner — Steven M Marsh
(74) Attorney, Agent, or Firm — Anthony J. Bourget (57) ABSTRACT A device and methods for holding a circular drain or circular gutter extension, including a connecting piece configured to connect to a drain or gutter extension, the connecting piece comprising a side portion arranged in a substantially circular configuration defining a flow chamber, at least a first frame segment positioned at a front of the side portion and extending at least partially into the flow chamber, and at least a first tab extending from an inner surface of the side portion into the flow chamber, and a stake connected to and extending outward from an outer surface of the side portion. The device is inserted or ratcheted upon the drain or tubing such that the tabs set into valleys of the tube for a secure connection such that when the stake is inserted into the ground the tubing is also secure.

21 Claims, 11 Drawing Sheets

DEVICE FOR HOLDING A DRAIN OR GUTTER DOWNSPOUT EXTENSION

CROSS-REFERENCE TO RELATED APPLICATIONS

This application is a continuation-in-part of, and claims the benefit and priority of co-pending U.S. patent application Ser. No. 15/932,745 filed on Mar. 16, 2018, for GUTTER DOWNSPOIUT EXTENSION HOLDING DEVICE, incorporated herein by reference as if fully reproduced herein.

BACKGROUND OF THE INVENTION

1. Field of the Invention

This invention relates to a downspout extension cover and holding device and devices that hold drains.

2. Background Information

Gutter downspouts commonly use an extension piece to assist in moving the rainwater to a position away from the house or building to which the gutter is attached. The extension typically fits into an elbow at the base of the downspout. The extension is sometimes friction-fit onto the downspout elbow or otherwise secured with a fastener. The extension extends outward from the house or building. In many cases the extension will detach from the elbow and blow away especially when there are heavy winds. The extension is often damaged by a weed trimmer or causes damage to a weed trimmer or other machines contacting the extension. The extension also includes sharp and sometimes hazardous edges. There have been a variety of devices used to attempt securing an extension into position or to cover the sharp edges, such as the device shown in U.S. Pat. No. 9,238,916. While some device have benefits, there is room for improvement.

SUMMARY OF THE INVENTION

In one aspect the invention is a device configured to keep a gutter downspout extension securely in place, and includes a sleeve or cap which slides over the end of the extension and includes a downward-extending ground stake for insertion of the device into the ground. The installed device prevents the downspout extension from separating from the gutter downspout elbow to which it is attached. Staking the device keeps the device connected to the extension, and keeps the extension connected to the downspout.

In a further aspect the invention includes a gutter extension connecting piece having side portions, including a bottom portion, where the side portions are arranged in a substantially rectangular configuration defining a flow chamber therethrough, a frame positioned at a front of at least one of the side portions and a tab extending rearward from the frame and into the flow chamber, the tab spanning a length which is shorter than a longest length of the frame, and a stake connected to and extending downward from the bottom portion. In one aspect the tab narrows rearwardly. In one aspect the tab and at least one of the side portions defines a channel. In one aspect the channel expands rearwardly. In a further aspect the sides join at respective corners and the corners are open such that respective corners of an inserted gutter extension are able to contact the respective corners of the connecting piece.

In a further aspect of the invention the device is made of a rigid plastic which resists damage due to weed trimmers or other equipment. In a further aspect the device of the present invention is made of a single piece of integrally connected substantially rigid plastic. In one aspect the device is made of polyvinyl chloride PVC.

In a further aspect the invention includes a set of 3 internal "tabs" which allow for easy insertion of the device onto the end of the downspout extension. The lower-most internal side of the device is smooth (i.e., the side closest to the stake does not include a tab) so that debris is free to flow from the extension and device without interruption.

In a further aspect the invention includes a device for holding a drain or gutter extension and having a side portion arranged in a substantially circular configuration defining a flow chamber therethrough, at least one frame segment positioned at a front of the side portion and extending into the flow chamber and having a maximum arch length, at least one tab positioned on an inner surface of the side piece and extending into the flow chamber, the tab having an arch length spanning a distance which is shorter than the maximum arch length, and a stake connected to and extending outward from an outer surface of the side portion.

The above partial summary of the present invention is not intended to describe each illustrated embodiment, aspect, or every implementation of the present invention. The figures and detailed description and claims that follow more particularly exemplify these and other embodiments and further aspects of the invention.

While the invention is amenable to various modifications and alternative forms, specifics thereof have been shown by way of example in the drawings and will be described in detail. It should be understood, however, that the intention is not necessarily to limit the invention to the particular embodiments, aspects and features described. On the contrary, the intention is to cover all modifications, equivalents, and alternatives falling within the spirit and scope of the invention and as defined by the appended claims.

DETAILED DESCRIPTION OF THE INVENTION

Figure 1:
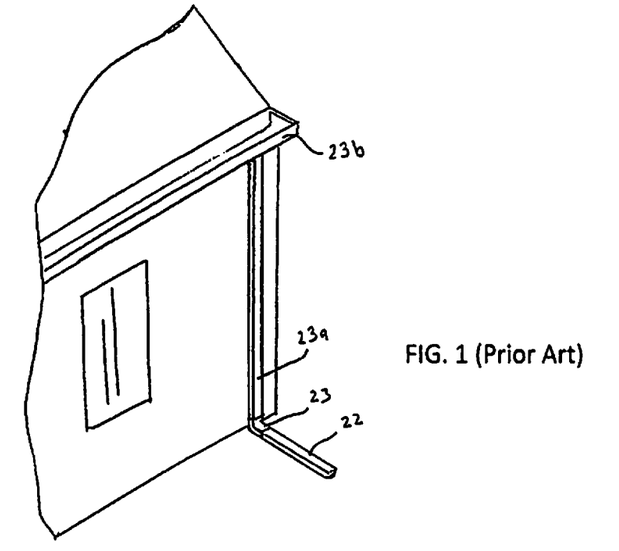
FIG. 1 is a perspective view of prior art showing a gutter extension connected to an elbow in turn connected to a downspout of a gutter system.

Referring to FIGS. 1-14, aspects of a device for connecting to a gutter extension in accordance with the invention are shown. Referring to FIGS. 15-24, aspects of an alternative device for holding a drain in accordance with a further embodiment of the invention are shown. Gutter extension holding device 20 includes a gutter extension connecting piece 24 and a stake 26. Connecting piece 24 is configured to connect to a gutter extension 22 (See FIG. 1, FIG. 2 and FIG. 3) which in turn typically connects to an elbow 23 at the base of a gutter downspout 23a or gutter system 23b of a house or building. The stake 26 is configured to pierce into the ground to hold device 20 into position while also securing the gutter extension to and against the elbow or house gutter downspout 23a. Connecting piece 24 secures to a terminal end or terminal portion of the gutter extension 22 as described below. Having the stake 26 secured into the ground anchors the terminal portion of the gutter extension 22 in a secure manner, preventing or lessening the tendency for the extension 22 to be detached from the elbow 23.

Figure 4:
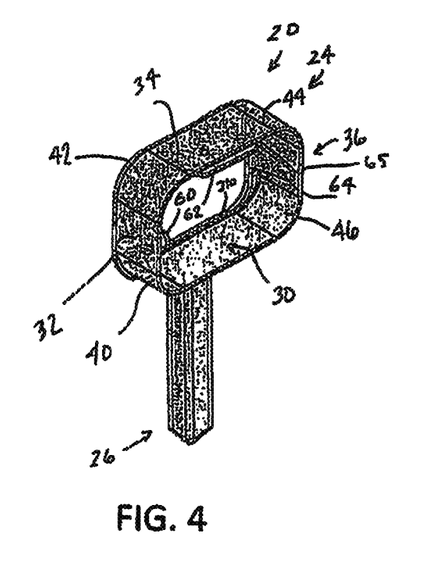
FIG. 4 is a reverse perspective view of the device of FIG. 2.

Referring to FIG. 4, which is a reverse or back-side perspective view of device 20, stake 26 connects to and extends downward from connecting piece 24 at a bottom side portion 30. Connecting piece 24 includes the bottom side portion 30, a left side portion 32, top side portion 34 and right side portion 36. The side portions 30, 32, 34, and 36 are arranged in a substantially rectangular configuration defining a flow chamber 38. The rectangular configuration is oriented to receive a terminal portion of the gutter extension which may be of a standard size. Flow chamber 38 receives a terminal portion of the extension 22 and allows water and debris from the gutter system 23b and extension 22 to freely pass through connecting piece 24. In one aspect the side portions 30, 32, 34, 36 are joined at relatively sharp angles or corners, and in other aspects as shown in FIG. 4 the side portions connect at rounded corners, such as at first corner portion 40, second corner portion 42, third corner portion 44 and fourth corner portion 46.

Figure 5:
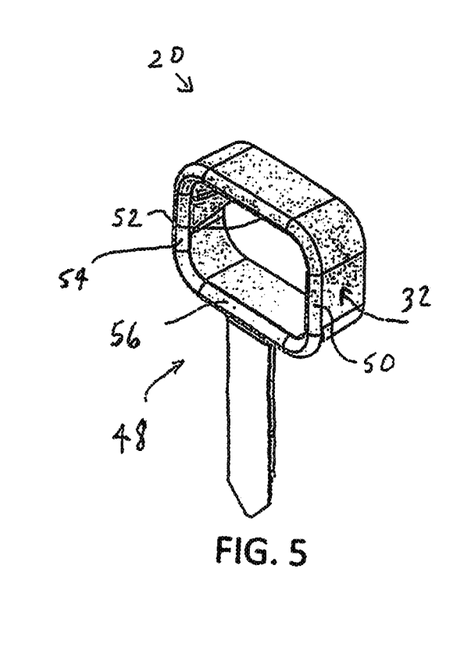
FIG. 5 is a perspective view of the device show in FIG. 4.
Figure 6:
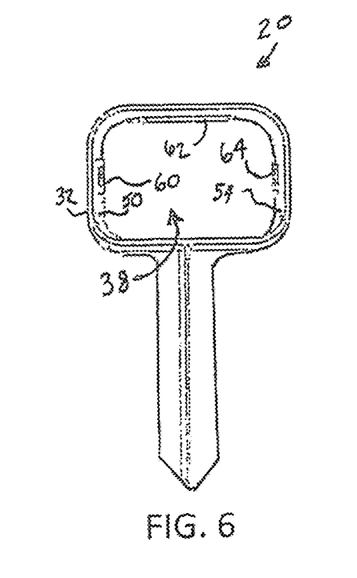
FIG. 6 is a rear view of the device of FIG. 2.

Referring to FIG. 5, connecting piece 24 further includes a first frame 50 which is positioned at a front of left side portion 32 and projects inward toward right side portion 36. A second frame 52 is positioned at a front of top side portion 34 and projects toward bottom side portion 30. A third frame 54 is positioned at a front of right side portion 36 and projects toward left side portion 32. In one aspect of the invention, a fourth frame 56 is positioned at a front of bottom side portion 30 and projects toward top side portion 34. In one aspect, fourth frame 56 comprises a small lip 31a which extends slightly above a top surface 31 of bottom side 30. Lip 31a in one aspect extends above surface 31 a distance equal to or substantially equal to a thickness of the material comprising one side of the extension piece 22 which is inserted into connecting piece 24. In this manner the lip 31a and inside surface 22a of the extension piece are flush or align along a common plane to present a smooth surface. Such smooth surface advantageously allows water and materials to freely exit the flow chamber 38 and avoid interruption or being trapped against connecting piece 24. Such smooth configuration lessens clogging of the gutter extension 22. But for such smooth or flush arrangement, leaves or other debris attempting to exit the extension piece would or could potentially catch against or along the front side of device 20. In other aspects, fourth frame 56 simply comprises a terminal front edge of bottom side portion 30 and does not include a lip 31a. In such "no-lip" configuration the terminal edge 25 of a bottom surface of the extension piece 22 when inserted into device 20 will be exposed to view from a front side 48 of device 20.

With reference to FIGS. 4-12, first frame 50 extends inward from left side portion 32 and includes a first tab 60. Tab 60 extends rearward from first frame 50 and into the flow chamber 38. Second frame 52 includes a second tab 62 extending rearward and third frame 54 includes a third tab 64 extending rearward. Tab 60, frame 50 and left side portion 32 define a first channel 70. Tab 62, frame 52 and top side portion 34 define a second channel 72. Tab 64, frame 54 and right side portion 36 define a third channel 74. As shown in FIG. 4, third tab 64 extends rearward a distance which is less than a depth of right side portion 36. In one aspect, tab 64 (and tabs 60, 62) tapers or narrows rearwardly as shown in FIG. 4. Tab 64 includes a rearward edge 65 which in one instance is rounded as shown. In one aspect, tab 64 (and/or tabs 60, 62) has a material thickness (represented by arrow "t" in FIG. 9) which is equal to or substantially equal to the thickness of right side portion 36 (and/or equal to or substantially equal to thickness "t" of left side portion 32 in the case of tab 60). In one aspect channel 70 spans from left side portion 32 to first tab 60 a distance configured to receive a front edge portion of a side of the extension piece 22 to be inserted into connecting piece 24 (or connecting piece 24 is inserted upon the extension piece).

The configuration of device 20 accommodates efficient insertion onto extension 22. Particularly, device 20 will firmly friction fit onto the terminal portion of an extension 22, yet such firm fitting is very easy to accomplish. In some instance an extension 22 will have jagged or bent or wrinkled edges such that an opening of the extension 22 will not be uniformly rectangular or will have some side walls or corners that are misaligned. The end portion of an extension 22 may also be deformed due to being stepped upon or otherwise the end portion becomes misshaped. Heretofore the misshaped terminal portion of the extension 22 makes insertion of an end cap device difficult or impossible, or requires the misshaped side portions to first be bent or smoothed back into the original rectangular configuration in order for a cap to be placed on the end of the extension 22. Device 20 is configured to allow for easy friction fit insertion of an extension 22 while automatically or simultaneously reforming or at least urging or partially urging the reformation of the terminal end of the extension 22 to be squared or rectangularly repositioned during the insertion of device 20 onto extension 22. In some aspects, sliding the extension 22 into the connecting piece 24 reforms edges of the extension without having to use tools. As is described further below, extension 22 friction fits into channels 70, 72, 74 despite irregularities that may exist at the terminal corner portions of the extension 22.

Figures 9, 10:
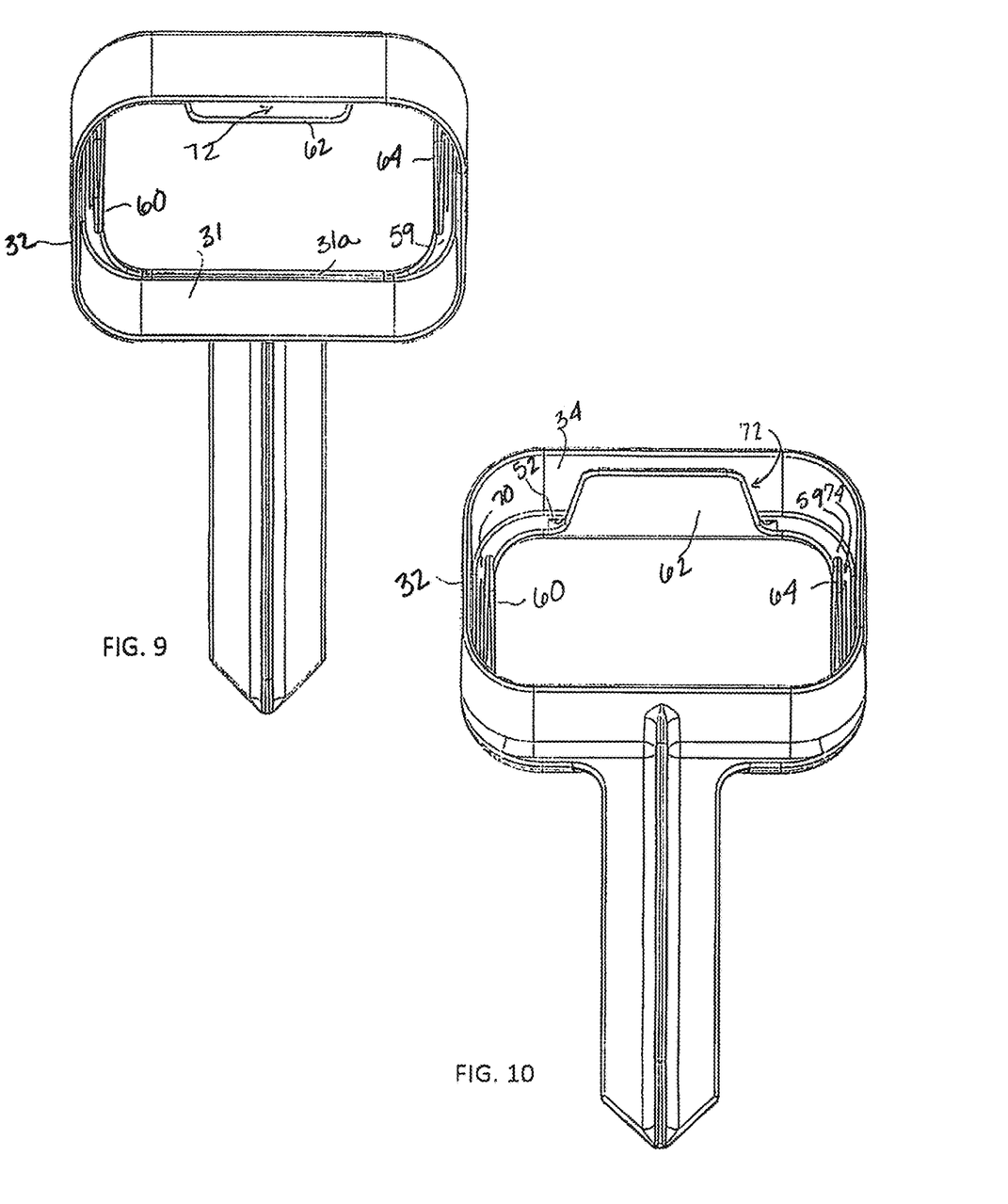
FIG. 9 is a top perspective view of the device of FIG. 2.
FIG. 10 is a bottom perspective view of the device of FIG. 2.
Figure 11:
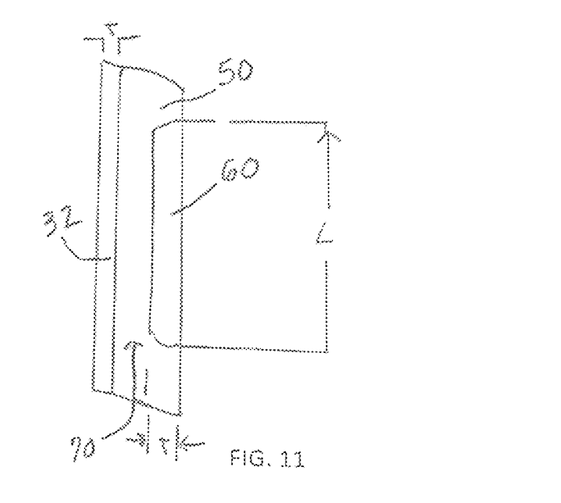
FIG. 11 is an enlarged partial rear view of aspects of the device of FIG. 2 in accordance with the invention.
Figure 12:
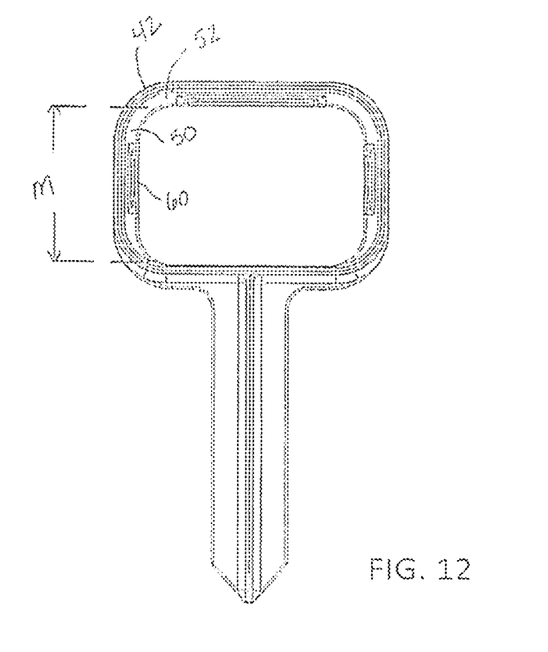
FIG. 12 is a rear view of the device of FIG. 2.

As shown in FIG. 9 and FIG. 10, first frame 50 has a length "M". It may be appreciated that frame 50 integrally connects with second frame 52. In the present example, the length "M" of first frame 50 spans from bottom side portion 30 to a lower edge of the second frame 52 connected to top side portion 34. In one aspect, first tab 60 has a length "L" which is less than or shorter compared to length "M". Such shortened length for first tab 60 accommodates for ease of insert of terminal portion of extension 22. Particularly, first frame 50 and second frame 52 are devoid of a tab element or elements at second corner portion 42. Such open area along the frame at corner portion 42 makes insertion of extension 22 relatively easy at such location even if the corresponding corner portion of extension 22 is misshaped. For instance, if the corresponding corner portion of extension 22 is bent or wrinkled, or if adjacent panels of extension 22 are oriented at a deformed or sharp angles, there is sufficient clearance at corner portion 42 to allow extension 22 to nonetheless insert into connecting piece 24. Further, channel 70 assists in guiding a panel of extension 22 into a secure position. In one aspect, the width of channel 70 will be narrow closer to front side 48 as compared to the width of channel 70 at a rear of the connecting piece 24. In one instance a slight taper is used to provide a relatively easy entry into the channel 70 while progressively narrowing to accommodate a gradual friction fit and tightening against sides of the inserted panel of extension 22. The width of channel 70 at or toward the front side 48 is configured to correspond to a standard material width of a panel of a typical extension 22. The channels in one aspect expand rearwardly (i.e., become wider closer to the rear of the device 20). In some aspects the thickness of the material of a side of an aluminum extension is 0.019 inches to 0.032 inches (with different thickness options, such as 0.019, 0.024, 0.027, 0.032). The channels 70, 72, 74 in some aspects are configured to receive an extension of any particular size thickness. The channels 70, 72, 74 defined above are likewise configured to receive panels of a typical extension 22 via friction fit. The tabs 62, 64 extending along respective frames 52, 54 also have a shorter length compared to the lengths of their respective frames 52, 54, so that corner portions 44, 46, 40 may also be devoid of tabs or elements that would otherwise impede insertion of extension into connecting piece 24.

In one aspect device 20 is made of hardened plastic, such a PVC or other rigid or substantially rigid material. Such hardened plastic accommodates aggressively inserting device 20 upon an end of extension 22 by relatively great force, if necessary, to align deformed panels or deformed corners/edges of extension 22 into alignment with the channels 70, 72, 74 of connecting piece 24. If necessary, the smooth hardened plastic allows a user to force the device 20 onto an extension without harm to the person's hand. The side portions 30, 32, 34, 36 operate in conjunction with tabs 60, 62, 64 to guide the inserted extension 22 into the channels 70, 72, 74. In one instance the terminal edges of an inserted extension 22 will abut against frame members 50, 52, 54 and optionally 56 if present. A user may apply force to the front side 48, via pounding upon connecting piece 24 with the palm of a hand if necessary, to easily and secure device 20 to extension 22. In many instances where extension 22 is not misshaped, insertion of device is swift and requires very little force yet results in a secure friction-fit connection. A user may hear the extension 22 bottom out against at least one or more the frame elements 50, 52, 54, 56.

Figure 7:
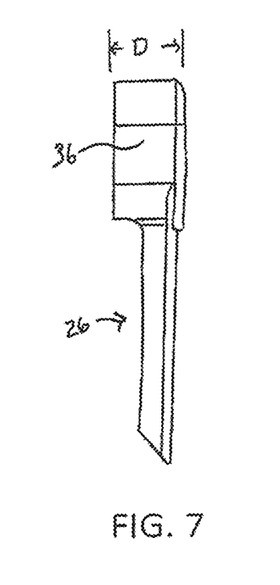
FIG. 7 is a left side view of the device of FIG. 2.
Figure 8:
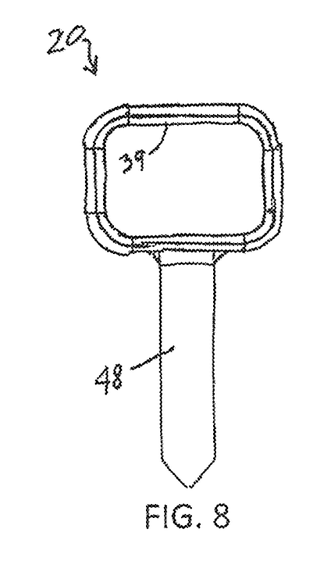
FIG. 8 is a front view of the device of FIG. 2.

In one aspect, the side portions 30, 32, 34 and 36 have a depth of about 1 to 1½ inches, spanning from front side 48 to rear. As shown in FIG. 7, depth is represented by arrow "D", and in that example is about 1¼ inches. Such depth provides sufficient or a desired depth of channels 70, 72, 74 to accommodate a sufficient or desired friction fit of extension 22. The stake 26 has a depth which is less than depth "D", and together with the connecting piece 24, device 20 has a total height of about 5½ to 7½ inches, and in the example of FIG. 7 about 6 inches. The rounded corner portions 40, 42, 44, 46 provide smooth aspects for safety protection, and the frame elements 50, 52, 54, 56 provide safety protection from a sharp terminal edges of extension 22. The hardened plastic provides a rigid structural protection to avoid or reduce crushing of a terminal portion of extension 22 such as by a person stepping upon or object contacting the terminal portion. Having the device 20 anchored into the ground via stake 26 provides further security to extension 22 and reduces or eliminates detachment of extension 22 from elbow 23. Having device 20 anchored into the ground via stake 26 also allows for a house-ward force to be applied against extension 22 to further secure extension 22 against elbow 23 and the house or building. Use of device 20 accommodates for easy retraction of stake 26 from the ground for swift removal of extension 22 from the elbow 23 in order to perform yard maintenance (mowing or trimming, etc) or repair. Device 20 allows for quick and effective reattachment of extension 22 to elbow 23 when maintenance or repair is completed.

Figure 2:
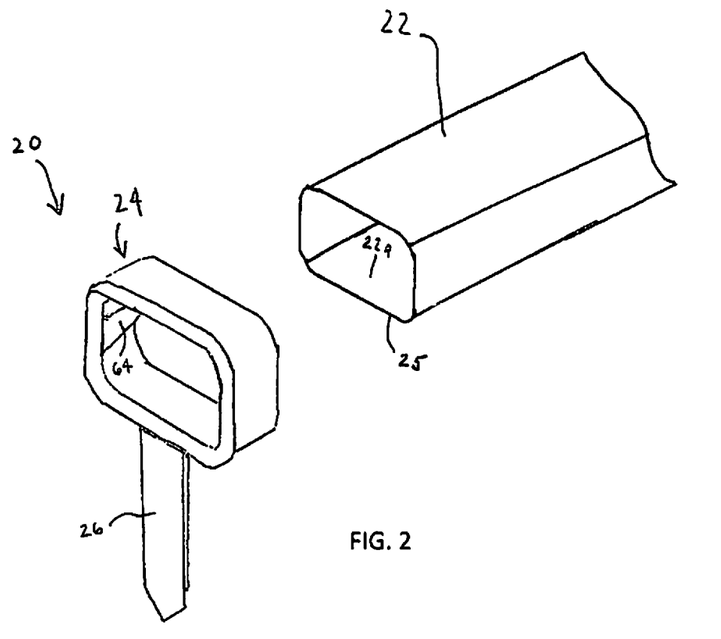
FIG. 2 is a perspective view of a device made in accordance with one aspect of the present invention and showing connection of the device to an extension or discharge pipe in one operational aspect of the invention.
Figure 3:
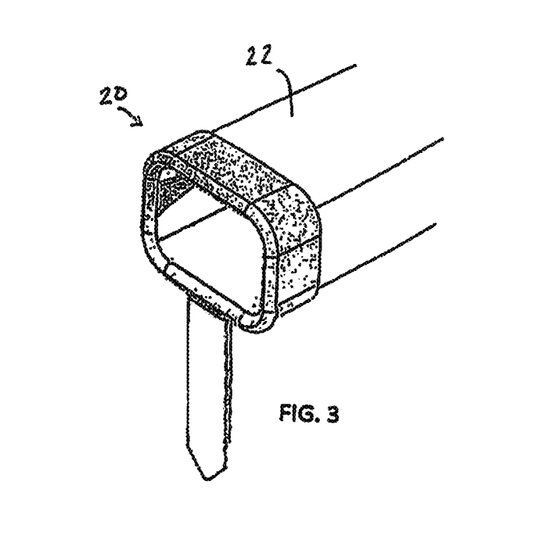
FIG. 3 is a perspective view of the device shown in FIG. 2 and connected to an extension.
Figure 13:
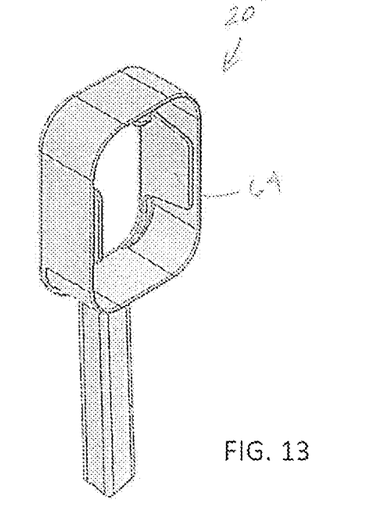
FIG. 13 is a rear perspective view of a device in accordance with a further aspect of the invention.
Figure 14:
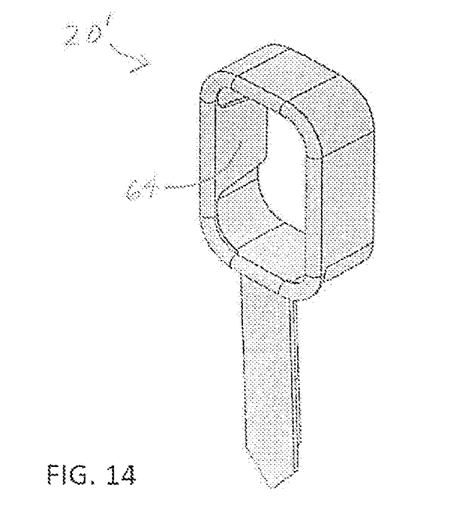
FIG. 14 is a perspective view of the device of FIG. 13.

In one aspect device 20 is configured to be placed upon the terminal portion of an extension 22 having a dimension of 3 inches by 4 inches, and oriented to lay as presented in FIG. 2. In other aspects, device 20 is configured to receive extensions 22 having greater or lesser dimensional measures, depending on the scale of gutter system being used. In a further aspect of the invention as shown in FIG. 13-14, device 20' is configured to receive an extension 22 in a primarily vertical orientation. Such vertically oriented device 20' may be configured to accommodate a standard 3 inches by 4 inches extension 22, or configured to receive extensions 22 greater or lesser dimensional measures. The device 20' includes a connecting piece which is the same or similar to the connecting piece 24 described above, yet being oriented in a relatively vertical configuration as shown.

A device for holding a drain in accordance with further embodiments of the invention are shown in reference to FIGS. 15-25. Drain holding device 120 includes a drain or gutter connecting piece 124 and a stake 126. Connecting piece 124 is configured to connect to a drain 122. The holding device 120 inserts into the ground via stake 126 to hold the drain 122 into position. Drain 122 may come in a variety of sizes, styles or designs, including a standard size 4 inch drain tile variety (in one instance of a variety complying with ASTM F667/F667M-16 (incorporated herein by reference). Device 120 is configured to slide upon and secure to a drain tube complying with these standards as of the effective date of the filing of this application. In some aspects drain 122 is a tubular structure made of rigid plastic with or without drain slots/holes. In other instances drain 122 is made of lighter grade plastic and is flexible and may also "accordion" or extend lengthwise. Drains 122 are commonly configured to connect lengthwise to adjacent drains 122 to create a long chain drain extending any desired length. In some aspects drains 122 have a locking mechanism at one end to receive a mating locking mechanism at the opposite end. Holding device 120 is configured to connect to and hold drains 122 as described below.

Figures 15, 16, 17, 18, 19:
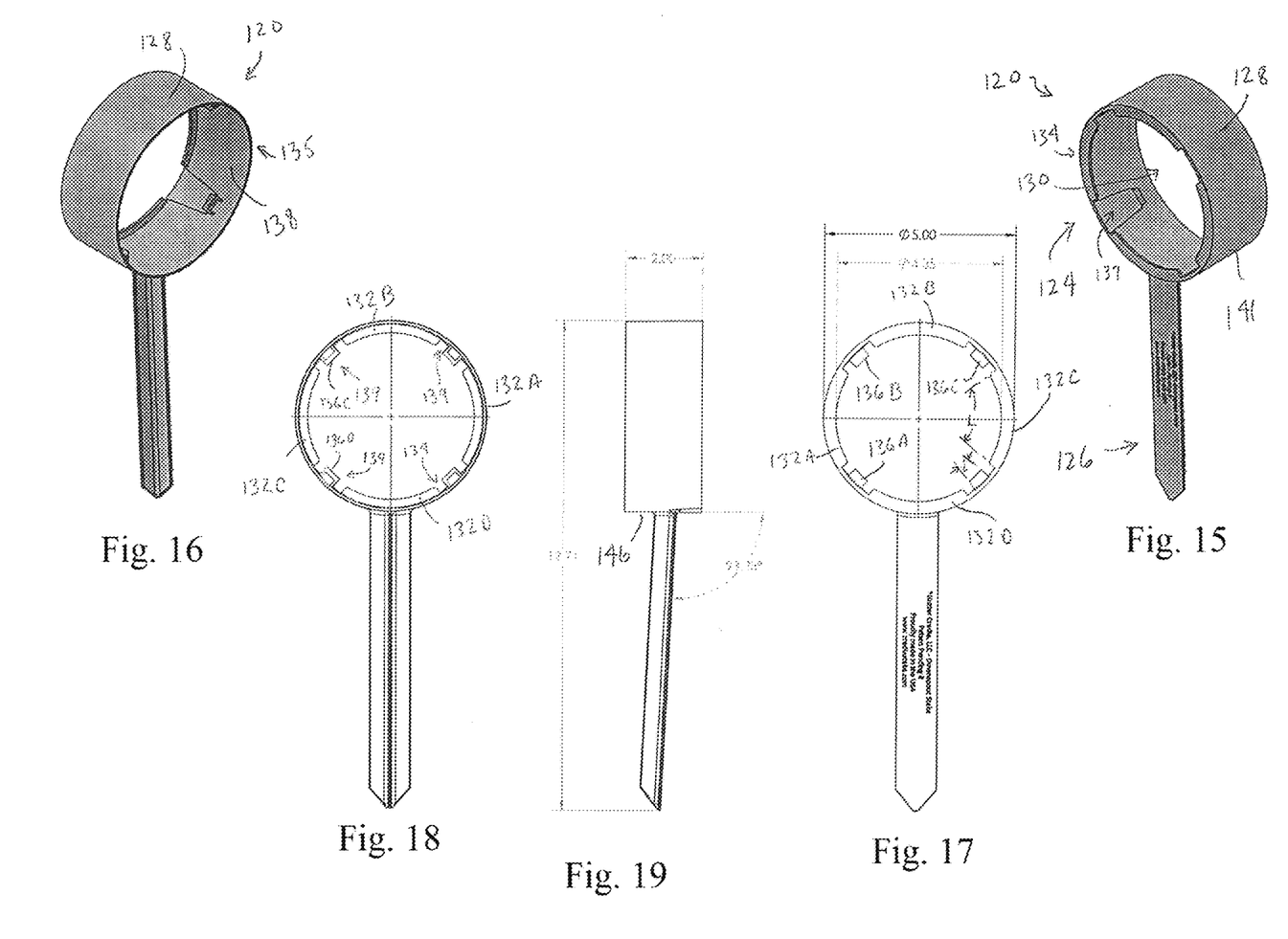
FIG. 15 is a perspective view of a device for holding a drain in accordance with a further embodiment of the invention.
FIG. 16 is a reverse perspective view of the device of FIG. 15.
FIG. 17 is a front view of the device of FIG. 15.
FIG. 18 is a rear view of the device of FIG. 15.
FIG. 19 is a side view of the device of FIG. 15.
Figure 20:
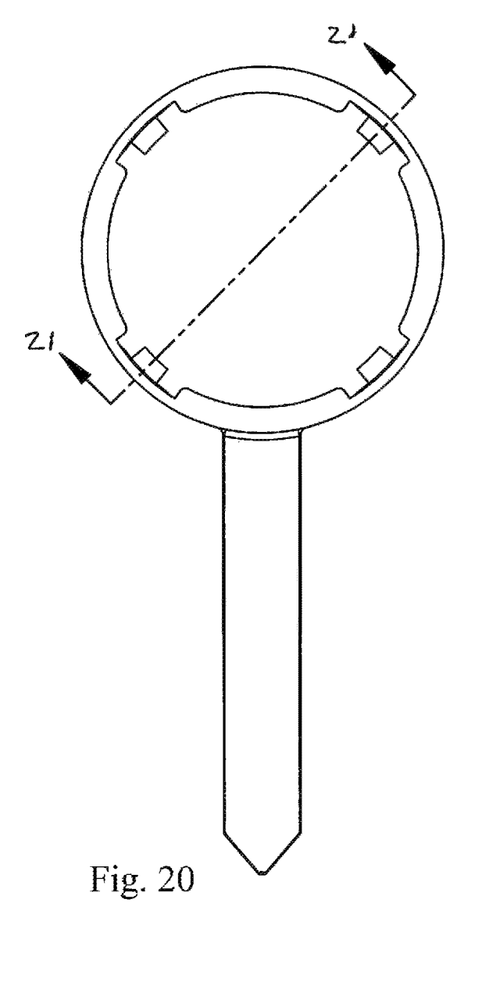
FIG. 20 is a front view of the device of FIG. 15.
Figure 21:
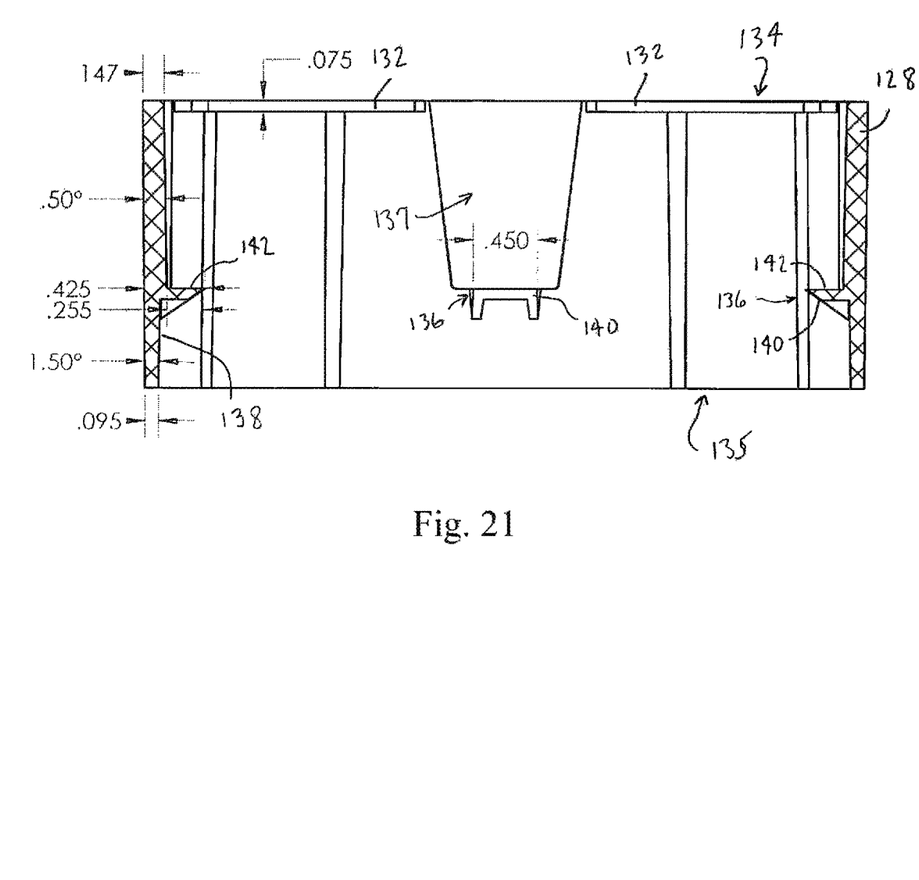
FIG. 21 is a section view taken along line 21-21 of FIG. 20.
Figure 22:
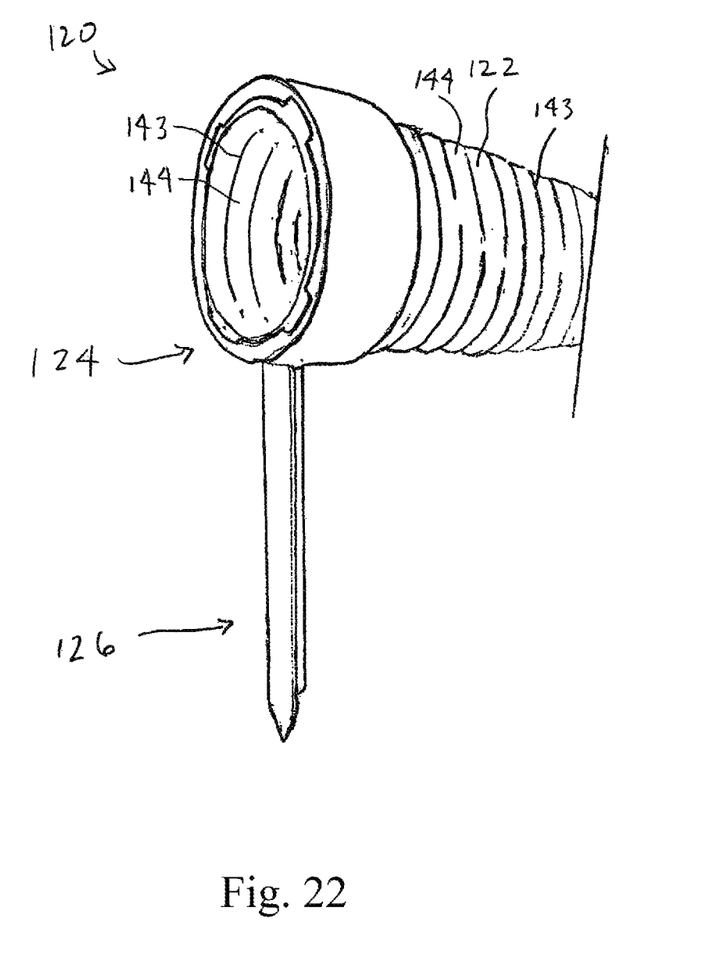
FIG. 22 is a perspective view of the device of FIG. 15 in a representative use application.

Referring to FIG. 15, which is a perspective view of drain holding device 120, connecting piece 124 includes a tubular side portion 128, the side portion 128 being arranged in a substantially circular configuration defining a flow chamber 130. A frame segment 132 extends partially into the flow chamber 130. In one aspect a frame segment 132 extends into the flow chamber 130 from multiple positions equally spaced about a front end 134 of the side portion 128. In the embodiment shown there are four frame segments 132A-D, with a segment 132 extending inward from each of a generally top, bottom, left and right positions of the front end 134. In one aspect the purpose of the frame segments 132 is to prevent the drain tube 122 from exiting through the front of connecting piece 124. A tab 136 extends from an inner surface 136 of the side portion 128 and into the flow chamber 130. In one aspect a tab 136 extends into the flow chamber 130 at each of multiple positions around the inner surface 138 of the side portion 128, approximately midway between front end 134 and rear end 135 of side portion 128. As shown in some aspects the tab 136 is positioned closer to a rear end 135 of connecting piece 124 as compared to a front end 134 of the connecting piece 124. As explained further herein such spacing accommodates insertion upon and securing about a drain tube 122, 122'. In one aspect tabs 136 are positioned in or align along spaces or gaps 139 defined between the frame segments 132 when viewed along the axis of the flow chamber 130. The tab 136 aligns along a path 137 extending rearward from the gap 139 (See FIG. 18). In one aspect the gaps 139 assist with efficient fabrication of the connecting piece 124. With reference to FIG. 17, frame segments 132, and particularly frame segment 132C has a maximum arch length represented by arrow "L" which spans generally in an arch-like manner around the perimeter of front end 134. Tab 136D has an arch length, such as length represented by arrow "i" spanning a distance which is shorter than maximum length "L". In one aspect of a process for manufacture of device 120, such shorter length "i" allows for a production molding component to retract or release from a corresponding molding component (i.e., were the length "i" greater than the gap length between adjacent frame segments 132, a forming mold would not be able to insert and release from front end 134 in order to form tab 136 (the frame segments themselves would prevent such entry or release)).

The tabs 136 provide an inclined surface 140 on the rear-facing side of the tab to allow a corrugated tubing 122 to pass over the tabs 136 and a flat surface 142 (front side planar surface) on the front-facing side to prevent tubing 122 from withdrawing once device 120 is slid upon tubing 122. The flat surface 142 (See FIG. 21) is oriented generally perpendicular to the inner surface 138. The inclined surface 140 forms an obtuse angle with respect to the inner surface 138 rearward of the tab 136. The tabs 136 further retain the device 120 to tubing 122 by engaging within a corrugation or valley 143 of the tube 122 (See FIG. 22). In one case tube 122 is a hard plastic tube 122 having three ridges 144 and three valleys 143 per 2 inch segment of tubing 122. The tab 136 sits within the second valley 143 as measured from the terminal edge of the tube 122, where the terminal edge of the tube 122 starts with a full ridge 144. Device 120 is configured such that the terminal edge of the tube 122 meets the inside surface of the frame segments 132 at the front of the connecting piece 124 as the tab 136 is set within the second valley 143. The tab 136 extends inward toward the axis of the flow chamber about ⅛ inches. Once device 120 is set into position upon the rigid tube 122, it is difficult to remove device 120. The combined device 120 and tube 122 may be anchored into the ground using stake 126 which secures the tube 122 into position. The frame segments 132 operate to provide a smooth finished edge covering the terminal end of tube 122. An additional device 120 may be connected to an opposite end of tube 122, or the opposite end of tube 122 may also be connected to a downspout, gutter extension or other output or drainage source.

The stake 126 is connected to and extends outward from an outer surface 141 of the side portion 128, thereby defining a part of the side portion 128 as a bottom 146 of the side portion 128. Referring to FIG. 19, in one aspect the downward extension of the stake 126 from the bottom 146 of the side portion 128 deviates slightly from a right angle to the axis of the flow chamber 130. In one aspect the stake 126 extends downward and slightly toward the rear of the side portion 128 at a 93.26 degree angle. In one aspect stake 126 has a length of 7 inches. In other aspects the stake 126 has a length of 7.71 inches, and together with the connecting piece 124, device 120 has a length of 12.71 inches, the connecting piece having a diameter of 5 inches. In one aspect the inner diameter of connecting piece 124 as measured from inner edge of frame 132 is 4.35 inches. Device 120 in other aspects has a connecting piece 124 made of different diameters and configured to hold or connect to different sized tubes.

Referring to FIG. 19, the tubular side portion 128 has a width of about 2 inches, an outer diameter of 5 inches, and an inner diameter of 4⅞ inches. The outer diameter of the black rigid tube 122 in one aspect is 4⅝ measured at a ridge 143 (corresponding to a size 4 inch pipe). The measure from the inner portion of one tab to an opposite tab is 4⅛ inches. In one aspect device 120 is made of a single piece of plastic and may include a variety of materials including PVC or other substances.

Figure 23:
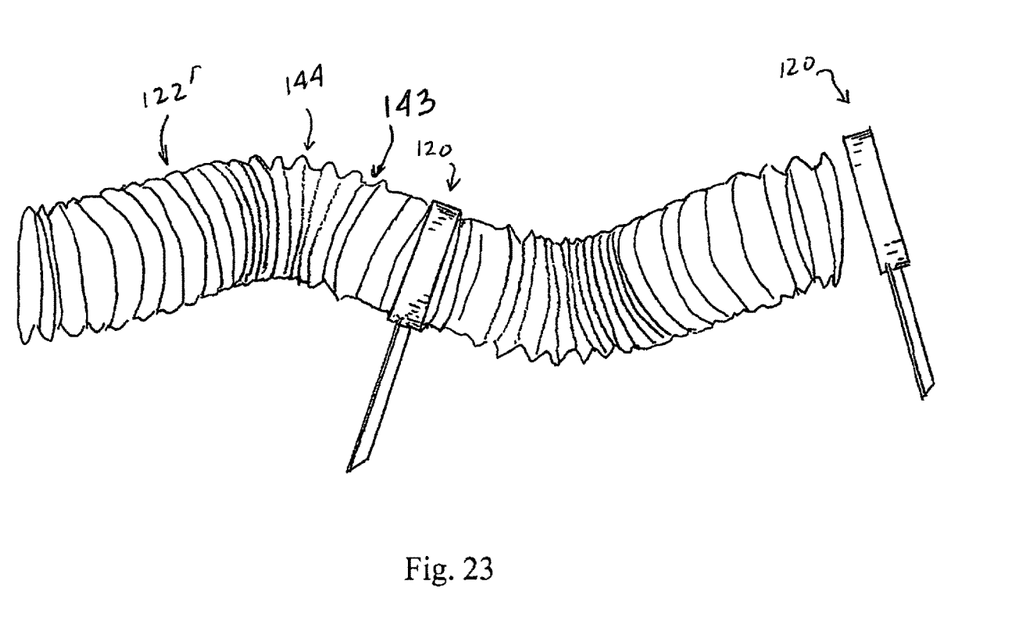
FIG. 23 is a side view of the device of FIG. 15 in a further representative use application.

In a further aspect device 120 is inserted upon a tube 122' (FIG. 23) which is a flexible tube having a series of ridges 144 and valleys 143 and is flexible such that tube 122' may bend easily. Such tubes 122' are typically made of softer plastic as compared to rigid tube 122 and will snake or flex as segments are compressed or expanded as generally shown in FIG. 23. Device 120 is configured to more easily insert upon and be removed from this softer structure of a tube 122' as compared to tube 122. For instance, a device 120 may easily slide upon and along a length of tube 122'. The tabs 136 ratchet along the length of tube 122' as device 120 is drawn lengthwise along the tube 122'. Several devices 120 may be slid along the length of tube 122' and staked into the ground or surface at desired intervals. This allows the tube 122' to be bent and aligned in various orientations and secured to the ground with device 120. Device 120 is universal in that it may be used in conjunction with the different types of tubing, including the rigid black drain tile varieties, the semi-rigid and flexible (telescoping) low-cost tube varieties. The device 120 in one aspect is inserted upon the rigid 122 and semi-rigid tubing 122' for use as draining tubes for topsoil landscaping, for instance.

In a further method aspect the invention includes securing in place a tubular extension piece of a downspout by utilizing the device 120. In one aspect the method includes passing the tube 122 through the back of connecting piece 124 (or passing the connecting piece 124 along the tube 122) until the frame segments 132 abut a terminal end of tube 122 (or set within a desired valley of tube 122'), rotating the tube until stake 126 is generally downwardly vertically disposed, and penetrate the ground with the stake 126. The stake 126 may insert into the ground at desired depths depending on the angle of pitch desired for setting the tube 122. In one aspect the stake is inserted at least ¾ the length of the stake.

Figure 24:
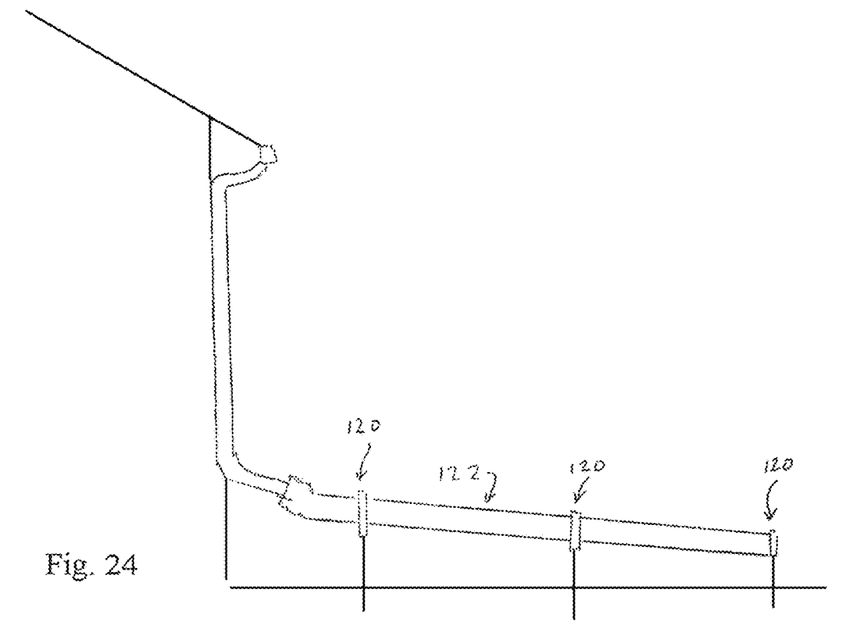
FIG. 24 is a side view of the device of FIG. 15 in a further representative use application.

A further method aspect includes connecting together multiple tubes 122', with device 120 attached to ends of adjacent tubes. Further aspect include insertion of multiple devices 120 along tube 122' for desired alignment and pitch as generally shown in FIG. 24. The devices 120 may be separated at desired distances along the chain of a single or multiple tubes 122, 122' and the stake 126 inserted at different depths to control the slope of the chain line. Multiple tubes 122' may be connected together and held into place with multiple devices 120, and the length of the connected tubes 122 may span several hundreds of feet or yards as desired.

Figure 25:
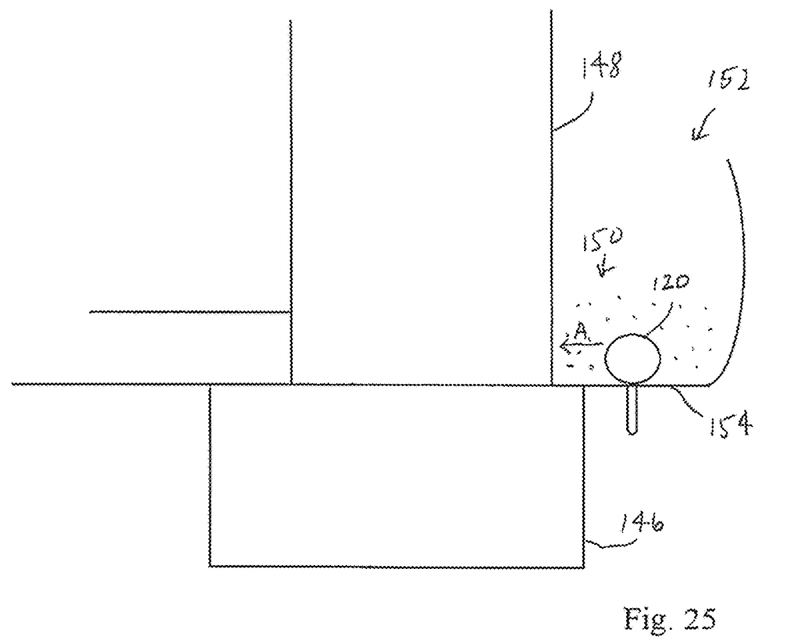
FIG. 25 is section view of the device of FIG. 15 in a further representative use application.

A further method aspect includes staking drain tile tubing 122 in place alongside a cement footing 146 of a building having a wall 148 to hold the tubing 122 in place while back-filling with sand 150 or gravel 150 in a trench 152 such that the drain tile tubing 122 does not move. FIG. 25 depicts a cross-section view of the device 120 which is connected to the tubing 122 and set into the ground 154 to secure the tubing 122. This assures the drain tile 122 abuts the wall 148 or the footing 146 to avoid a scenario in which water running down the outside of a wall might not seep into the drain tile tube 122 if the tube becomes separated from the wall or footing. The tubing 122 and device 120 may be adjusted along the Arrow A shown in FIG. 25 to secure the tubing 122 closer to the wall 148 or footing 146 as desired. Drain tubing 122 is typically installed around the perimeter of the structure. Use of device 120 allows for a single workman to place and secure the tube 122 into position with assurance that back-filling will not alter the path of the tube upon the back-filling process. Otherwise, a second or third worker often must also be positioned in the ditch and hold the tubing 122 into position during back-fill. A further aspect of the invention includes backfilling around a foundation of a building structure, including connecting a tubing 122 to a device 120 of the present invention, securing the tubing 122 into the ground about the foundation, and backfilling dirt upon the tubing 122 adjacent the foundation.

It should be understood, of course, that the foregoing relates to exemplary embodiments of the invention and that modifications may be made without departing from the spirit and scope of the invention as set forth in the following claims.

What is claimed is:

1. A device for holding a circular drain or circular gutter extension, the device comprising:
   a connecting piece configured to connect to a drain or gutter extension, the connecting piece comprising:
      a side portion arranged in a substantially circular configuration defining a flow chamber;
      at least a first frame segment positioned at a front of the side portion and extending at least partially into the flow chamber; and
      at least a first tab extending from an inner surface of the side portion into the flow chamber; and
   a stake connected to and extending outward from an outer surface of the side portion.

2. The device of claim 1 where the side portion is circular and is configured to receive a standard size 4 inch drain or gutter extension within the flow chamber.

3. The device of claim 1 where the connecting piece further comprises at least a second tab extending from the inner surface of the side portion into the flow chamber.

4. The device of claim 1 where the connecting piece further comprises at least a second frame segment positioned at a front of the side portion and extending at least partially into the flow chamber, the first segment and the second segment defining a gap, the first tab aligned along a path extending rearward from the gap.

5. The device of claim 4 where the gap spans a maximum gap length, the first tab having a total length that is shorter than the maximum gap length.

6. The device of claim 1 where the side portion has a total width, the first tab positioned from the front of the side portion a distance at least half the total width.

7. The device of claim 1 where the first tab has a front side planar surface oriented generally perpendicular to the inner surface.

8. The device of claim 1 where the first tab has a rear planar surface which is angled such that the rear planar surface forms an obtuse angle with respect to the inner surface rearward of the first tab.

9. The device of claim 1 where the connecting piece further comprises at least a second tab, third tab and fourth tab extending from the inner surface of the side portion into the flow chamber.

10. The device of claim 1 configured to receive a standard size 4 inch drain tube made of rigid plastic and having at least a first and second circular rib separated by a first valley and a third circular rib separated from the second circular rib by a second valley, the first tab of the device positioned inward from the front of the side portion such that the first tab inserts into the second valley upon insertion of the drain tube within the connecting piece.

11. The device of claim 10 where the drain tube includes a tube made in accordance with ASTM F667/F667M—16 and a terminal edge of the drain tube abuts a rearward surface of the at least a first frame segment when the device is fully inserted onto the tube.

12. The device of claim 1 configured to receive a standard size 4 inch drain tube made of semi-rigid plastic and having a series of circular ribs separated by respective valleys, the first tab of the device configured to insert into the respective valleys upon insertion of the drain tube within the connecting piece.

13. The device of claim 11 where the connecting piece is configured to slide along an entirety of a maximum length of the drain tube.

14. A device for holding a circular drain or circular gutter extension, the device, comprising:
   a connecting piece configured to connect to a circular drain or circular gutter extension, the connecting piece comprising:
      a tubular side portion defining a flow chamber passing therethrough;
      at least a first tab extending from an inner surface of the side portion into the flow chamber; and
   a stake connected to and extending outward from an outer surface of the side portion.

15. The device of claim 14 where the side portion has a total width, the first tab positioned from a front edge of the side portion a distance at least half the total width.

16. The device of claim 15 where the total width has a measure of at least 1.5 inches and the first tab is positioned from the front edge a distance of at least 1.25 inches.

17. The device of claim 14 having at least four tabs extending from the inner surface of the side portion into the flow chamber.

18. The device of claim 14 further comprising at least a first frame segment positioned at a front of the side portion and extending at least partially into the flow chamber.

19. The device of claim 14 where the tubular side portion has an inner diameter of at least 4 inches.

20. The device of claim 14 where the device is made of a single piece of integrally connected substantially rigid plastic.

21. A device for holding a circular drain or circular gutter extension, the device comprising:
- a connecting piece configured to connect to a drain or gutter extension, the connecting piece comprising:
  - a side portion arranged in a substantially circular configuration defining a chamber for receiving the circular drain or gutter extension, the chamber defining a central longitudinal axis passing therethrough;
  - at least a first frame segment positioned at a front of the side portion and extending toward the central longitudinal axis and having a terminal edge which faces the central longitudinal axis; and
  - at least a first tab extending from an inner surface of the side portion toward the central longitudinal axis; and
- a stake connected to and extending outward from an outer surface of the side portion.

* * * * *